US00PP27254P3

(12) United States Plant Patent
Olesen et al.

(10) Patent No.: US PP27,254 P3
(45) Date of Patent: Oct. 11, 2016

(54) ***CLEMATIS* PLANT NAMED 'EVIPO070'**

(50) Latin Name: *Clematis viticella*
Varietal Denomination: Evipo070

(71) Applicants: Mogens Nyegaard Olesen, Fredensborg (DK); Raymond Evison, St. Sampsons (GB)

(72) Inventors: Mogens Nyegaard Olesen, Fredensborg (DK); Raymond Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 131 days.

(21) Appl. No.: 14/121,292

(22) Filed: Aug. 15, 2014

(65) Prior Publication Data

US 2016/0050835 P1 Feb. 18, 2016

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

"Perfection by Poulsen—*Clematis* Main Varieties 2013" (3 pgs total).*

* cited by examiner

*Primary Examiner* — Susan McCormick Ewoldt

(57) ABSTRACT

A new *Clematis* plant with a compact growth habit, profuse, red-purple flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

1 Drawing Sheet

Botanical classification: Genus: *Clematis*. Species: *viticella*.

Variety denomination: 'Evipo070'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both of the parent varieties are non-patented.

The two parents were crossed during the summer of 2000 and the resulting seeds were planted the following winter in a controlled environment in Guernsey, Channel Islands. The new variety named 'Evipo070' originated as a single seedling from the stated cross.

The new *clematis* plant may be distinguished from its female seed parent and male pollen parent by the following characteristics. The male pollen parent has larger flowers and fewer flower buds than the claimed plant. The seed parent is more compact than the claimed plant.

The objective of the hybridization of this *clematis* plant was to create a new and distinct variety for nursery culture with unique qualities such as:

1. Uniform and abundant red-purple flowers;
2. Vigorous and compact growth, making the variety suitable for container culture;
3. Good flowering characteristics without vernalization; and
4. Improved disease resistance.

This combination of qualities was lacking in *clematis* plants that were in commercial cultivation and the qualities have been substantially achieved in the new variety.

'Evipo070' was selected by Mogens N. Olesen and Raymond J. Evison in their *clematis* development program in the Channel Islands, United Kingdom in 2001. Asexual reproduction of 'Evipo070' by means of vegetative cuttings and traditional layering was first performed by Mogens N. Olesen and Raymond J. Evison in the nursery during the summer of 2001. This initial and subsequent asexual propagations have demonstrated that the characteristics of 'Evipo070' are true to type and are transmitted from one generation to the next.

BRIEF DESCRIPTION OF THE DRAWING

The accompanying color illustration shows as true as is reasonably possible to obtain in color photographs of this type the typical characteristics of the buds, flowers, leaves, and stems, of 'Evipo070'. Specifically illustrated in the drawing are flowers at various stages of development, flower in parts, leaves, and stems.

DETAILED DESCRIPTION OF THE VARIETY

The following is a detailed description of 'Evipo070', as observed in its growth throughout the flowering period in open air cultivation in Yamhill County Oreg. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the *clematis* variety 'Evipo018' described and illustrated in U.S. Plant Pat. No. 16,267 issued Feb. 21, 2006 are compared to 'Evipo070' in Chart 1.

CHART 1

| | 'Evipo070' | 'Evipo018' |
|---|---|---|
| Flower diameter | 130 mm | 100 to 120 mm |
| General tonality of flower color | Red-Purple Group 61A with intonations of Red-Purple Group 61B. | Red-Purple Group 71A |
| Tepal count | 6 | 6 |

FLOWER AND FLOWER BUD

Blooming habit: Continuous. The natural flowering period is generally from May to September.

Flower bud:
- *Size*.—Normally 26 mm in length. Bud diameter is 9 mm.
- *Bud form*.—Long, campanulate.
- *Bud color*.—Greyed-Orange Group 177A & Yellow-Green Group 145A.

Peduncle:
- *Surface texture*.—Smooth.
- *Length*.—On average 80 mm.
- *Width*.—2 mm.
- *Color*.—Greyed-Purple Group 187A & Yellow-Green Group 145A.
- *Strength*.—Moderately strong.

Receptacle:
- *Surface texture*.—Smooth.
- *Shape*.—Funnel.
- *Size*.—4 mm (h)×3 mm (w).
- *Color*.—Yellow-Green Group 145A.

Flower arrangement:
- *Location on vine*.—New growth and overlapping.
- *Borne*.—Singly.
- *Aspect*.—Flowers are oriented upwards.

Flower bloom:
- *Size*.—On average, flowers are 130 mm in diameter and 25 mm in depth.
- *Profile*.—Open flowers are flat.
- *Fragrance*.—None.
- *Lasting quality*.—Flowers normally remain 6 days on the plant.

Tepals:
- *Tepal color*.—Upon opening, the upper surface is Red-Purple Group 61A with intonations of Red-Purple Group 61B. The lower surface is Greyed-Purple Group 186C with intonations of Greyed-Purple Group 187A in a central bar. After opening, the upper surface is Red-Purple Group 61A with intonations of Red-Purple Group 61B. The lower surface is Purple Group 75A with a central bar Greyed-Purple Group 187A.
- *Quantity*.—Normally 6 tepals.
- *Size*.—65 mm in length by 35 mm wide.
- *Shape*.—Individual tepal shape elliptic. The tepal apex is mucronate. The tepal base is acute.
- *Apex recurvature*.—Slight.
- *Tepal cross section*.—Reflexed slightly.
- *Margins*.—Entire. Weak undulations of margin observed.
- *Persistence*.—Tepals drop off cleanly.

Reproductive organs:
- *Arrangement*.—Open.
- *Pollen*.—None observed.
- *Anthers*.—Size: 6 mm in length. Color: Yellow-Green Group 150D. Quantity: On average, 40.
- *Filaments*.—Color: Red-Purple Group 71A at base, becoming Green-White Group 157B at the middle and upper portion. Length: 6 mm.
- *Pistils*.—Quantity: On average, 20.
- *Stigmas*.—Inferior in location relative to the length of the filaments and the height of the anthers.
- *Styles*.—Color: Green-White Group 157A. Length: 9 mm.

Seed head characteristics: None observed.

PLANT

Plant form: Climbing.

Plant growth: Moderate and compact.

Size: Seasons growth attains 1 meters in height. Average spread is 50 cm.

Stems:
- *Color*.—Juvenile stems are Yellow-Green Group 146B. Mature stems are Greyed-Orange Group 175A.
- *Internodes*.—On average, 85 cm between nodes.
- *Length*.—Normally 30 cm from the base of the plant to the flowering portion of the stem.
- *Diameter*.—Normally 3 mm.
- *Texture*.—Mature stems are ribbed.

Plant foliage:
- *Leaf characteristics*.—Deciduous.
- *Arrangement*.—5 leaflet pinnate, opposite.
- *Leaf size*.—Compound leaves are normally 160 mm (l)×120 mm (w). Leaflets are normally 45 mm (l)×2 mm (w).
- *Abundance*.—On average 4 leaves per 10 cm of stem.
- *Leaf color*.—Juvenile upper Yellow-Green Group 144A with Greyed-Orange Group 147A at margins. Juvenile lower Yellow-Green Group 144A. Mature upper Yellow-Green Group 146A. Mature lower Yellow-Green Group 146B.
- *Stipules*.—Absent.
- *Petioles*.—Size: Normally 50 mm in length by 1 mm diameter. Texture: Smooth. Color: Greyed-Purple Group 183A.
- *Petiolule*.—Size: 12 mm long and 1 mm diameter. Texture: Smooth. Color: Greyed-Purple Group 183A.
- *Leaflet shape*.—Generally aristate. The base is rounded. The apex is acute.
- *Margin*.—Entire.
- *Surface*.—The upper side is smooth. The lower side is smooth.
- *Thickness*.—Moderate.
- *Glossiness*.—Somewhat glossy.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo070', substantially as described and illustrated, due to its abundant red-purple flowers with good keepability, attractive long lasting foliage and compact growth, year round flowering under glasshouse conditions, suitability for production from softwood cuttings in pots, durable flowers and foliage which make the variety suitable for distribution in the floral industry.

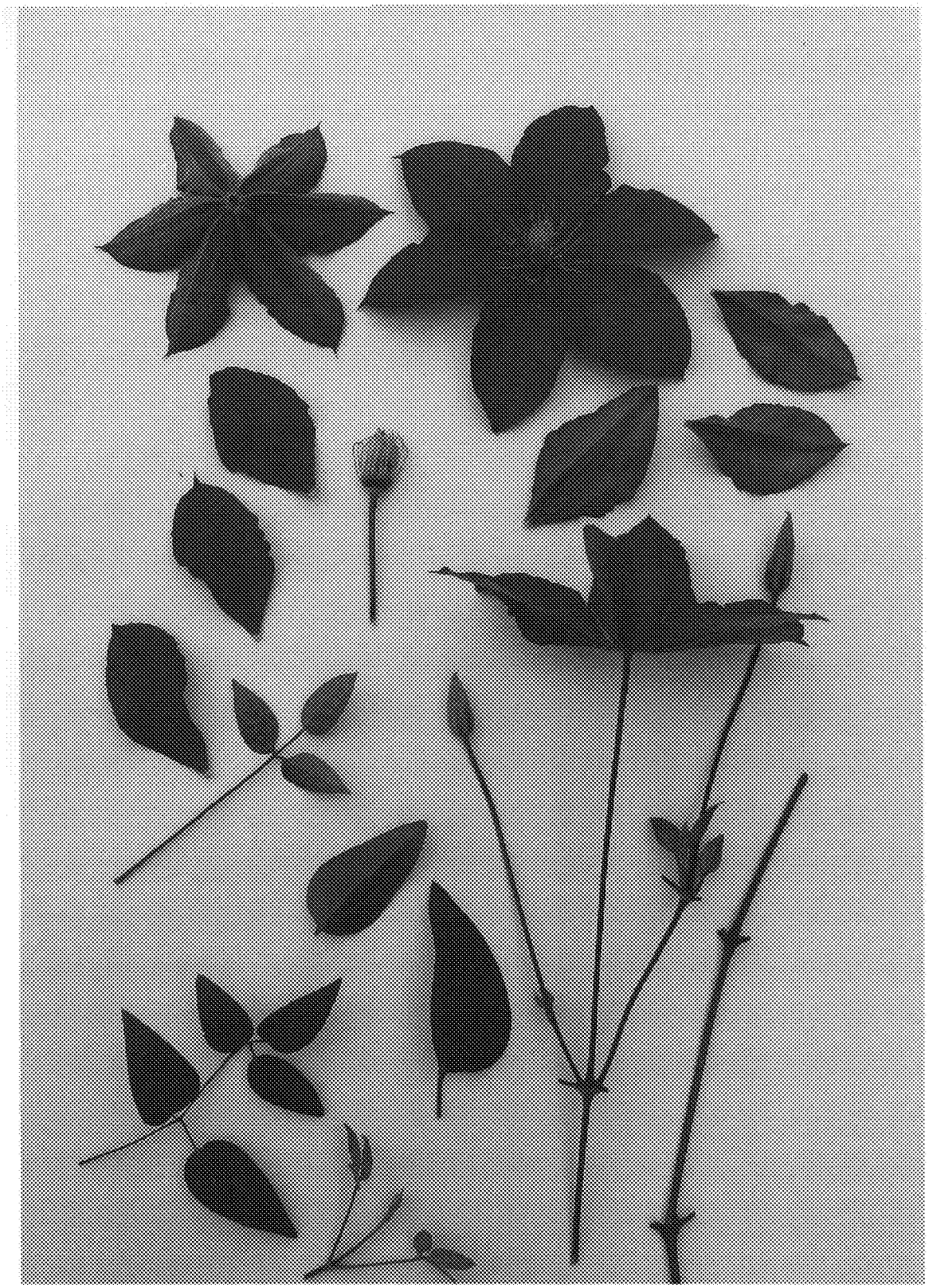

* * * * *